United States Patent [19]

Yamakawa et al.

[11] Patent Number: 4,569,748
[45] Date of Patent: Feb. 11, 1986

[54] OXYGEN-SENSOR

[75] Inventors: Michihiro Yamakawa, Kariya; Takao Akatsuka, Aichi; Masao Kawaguchi, Toyota; Jiro Nakano, Okazaki; Takao Ishibashi, Toyota, all of Japan

[73] Assignees: Nippondenso Co., Ltd., Kariya; Toyota Jidosha Kabushiki Kaisha, Toyota, both of Japan

[21] Appl. No.: 731,521

[22] Filed: May 7, 1985

[30] Foreign Application Priority Data

May 7, 1984 [JP] Japan .............. 59-66876[U]

[51] Int. Cl.⁴ ........................................... G01N 27/58
[52] U.S. Cl. .................... 204/429; 204/427; 204/428
[58] Field of Search ................ 204/1 S, 427, 428, 429

[56] References Cited

U.S. PATENT DOCUMENTS

| 447,940 | 12/1982 | Fujimoto et al. | 204/427 |
| 4,076,608 | 2/1978 | Fujishiro et al. | 204/427 |
| 4,141,813 | 2/1979 | Kita et al. | 204/428 |
| 4,189,355 | 2/1980 | Fujishiro et al. | 204/427 X |

FOREIGN PATENT DOCUMENTS

| 2733906 | 2/1978 | Fed. Rep. of Germany | 204/428 |
| 57-178152 | 11/1982 | Japan | 204/427 |
| 58-16144 | 3/1983 | Japan | 204/427 |

Primary Examiner—G. L. Kaplan
Attorney, Agent, or Firm—Cushman, Darby & Cushman

[57] ABSTRACT

An oxygen sensor according to the present invention comprises a tumbler-shaped solid electrolytic element formed of an oxygen-ion-conductive metal oxide. A first electrode and a lead electrically connected thereto are formed on the outer peripheral surface of the element which is exposed to exhaust gas. A second electrode is fixed to the inner peripheral surface of the element which is exposed to the atmosphere. The element is held by a ring-shaped metallic holder. The holder and the first electrode are electrically insulated from each other. A conductive metallic pipe member is disposed between the element and the holder. One end of the pipe member is electrically connected to the lead by means of a conductive metal ring. A partition wall extends integrally from one end of the pipe member, defining between its inner surface and the other peripheral surface of the element a space for housing the conductive metal ring between the pipe member and the lead. A seal member is interposed between the outer peripheral surfaces of the pipe member and the partition wall and the inner peripheral surface of the holder. The seal member is formed by compacting a powdered electrial insulating material.

6 Claims, 12 Drawing Figures

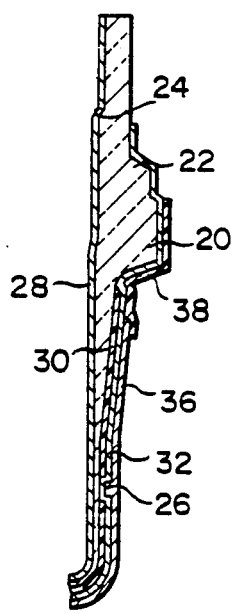
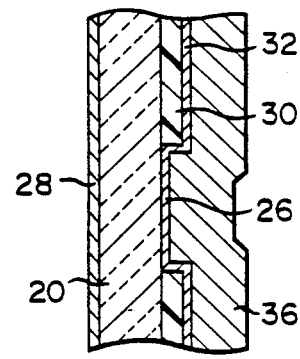
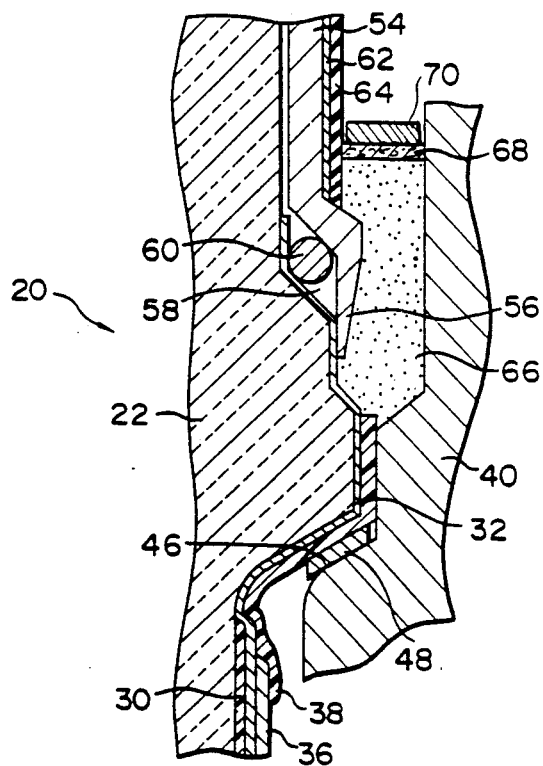

OXYGEN SENSOR

BACKGROUND OF THE INVENTION

The present invention relates to an oxygen sensor for detecting the oxygen content of a subject gas to be measured, and more specifically to an oxygen sensor adapted to detect the oxygen content of exhaust gas from an internal combustion engine for the control of the air-fuel ratio of an air-fuel mixture used in the engine.

Oxygen sensors of this type are disclosed in, for example, Japanese Patent Disclosure No. 178152/82, Japanese Patent Publication No. 16144/83, and U.S. application Ser. No. 447,940. These prior art oxygen sensors are provided with a solid electrolytic element formed of an oxygen-ion-conductive metal oxide. The element is in the form of a tumbler closed at one end and open at the other end. A first electrode is fixed to the outer peripheral surface of the element on the closed end side thereof. The outer peripheral surface of the element, on the first electrode side thereof, is exposed to a subject gas to be measured. On the other hand, a second electrode is fixed to the inner peripheral surface of the element, which is exposed to a reference gas.

A metallic holder is disposed on the open end side of the element so as to surround the same. The holder, which serves to hold the element, is electrically insulated from the first electrode. A conductive member is disposed at the open end portion of the element, located between the element and the holder. The conductive member is electrically insulated from the holder. The conductive member abuts against a lead which is formed on the outer peripheral surface of the element so as to be connected to the first electrode. Thus, the conductive member is electrically connected to the first electrode through the lead.

Further, a seal member is disposed in the holder, whereby the gap between the inner peripheral surface of the holder and the outer peripheral surface of the element is filled up for airtightness. The seal member is formed by compacting a powdered electrical insulating material such as talc.

The oxygen sensor described above is designed so that if a predetermined voltage is applied between the first and second electrodes, an electric current proportional to the oxygen content of the subject gas flows between the first and second electrodes. Thus, the oxygen content of the subject gas can be measured by detecting the current value.

In the above-mentioned oxygen sensor, however, the seal member filling up the gap between the inner peripheral surface of the holder and the outer peripheral surface of the element is formed by compacting a powdered material and is therefore liable to be reduced to powder. If the seal member crumbles, the resultant powder may possibly penetrate the junction between the conductive member and the lead, thereby cutting the electrical connection between the conductive member and the lead. As a result, it becomes impossible to apply a voltage between the first and second electrodes, so that the function of the oxygen sensor cannot be securely maintained.

SUMMARY OF THE INVENTION

The object of the present invention is to provide an oxygen sensor in which a seal member is prevented from ruining the electrical connection with a first electrode, thereby ensuring the maintenance of the sensor function.

The above object may be achieved by an oxygen sensor according to the present invention which comprises a solid electrolytic element formed of an oxygen-ion-conductive metal oxide and having the shape of a tumbler closed at one end and open at the other end, the outer and inner peripheral surfaces of the solid electrolytic element being exposed to a subject gas to be measured and a reference gas, respectively, a first electrode fixed to the outer peripheral surface of the solid electrolytic element on one end side thereof, a second electrode fixed to the inner peripheral surface of the solid electrolytic element, an insulated lead put on the outer peripheral surface of the solid electrolytic element, electrically connected to the first electrode, a metallic holder surrounding the other end portion of the solid electrolytic element to hold the same, the holder being electrically insulated from the first electrode, a conductive member disposed on the outer peripheral surface of the solid electrolytic element and electrically connected to the lead, a seal member for filling up the gap between the outer peripheral surface of the solid electrolytic element and the inner peripheral surface of the holder, the seal member being formed by compacting a powdered electrical insulating material, and partitioning means for separating the junction between the lead and the conductive member from the seal member.

According to the oxygen sensor of the present invention, the electrical junction between the conductive member and the lead is separated from the seal member by the partitioning means, so that the powdered insulating material of the seal member can securely be prevented from penetrating the junction. Thus, the electrical connection with the first electrode can be maintained for improved durability of the oxygen sensor without allowing the powder from the seal member to cut the electrical connection between the conductive member and the lead.

BRIEF DESCRIPTION OF THE DRAWINGS

FIG. 2 is a partial sectional view of a solid electrolytic element in the oxygen sensor of FIG. 1;

FIG. 3 is an enlarged view corresponding to section III of FIG. 1;

FIG. 4 is an enlarged view corresponding to section IV of FIG. 1;

DETAILED DESCRIPTION OF THE PREFERRED EMBODIMENTS

Figure 1:
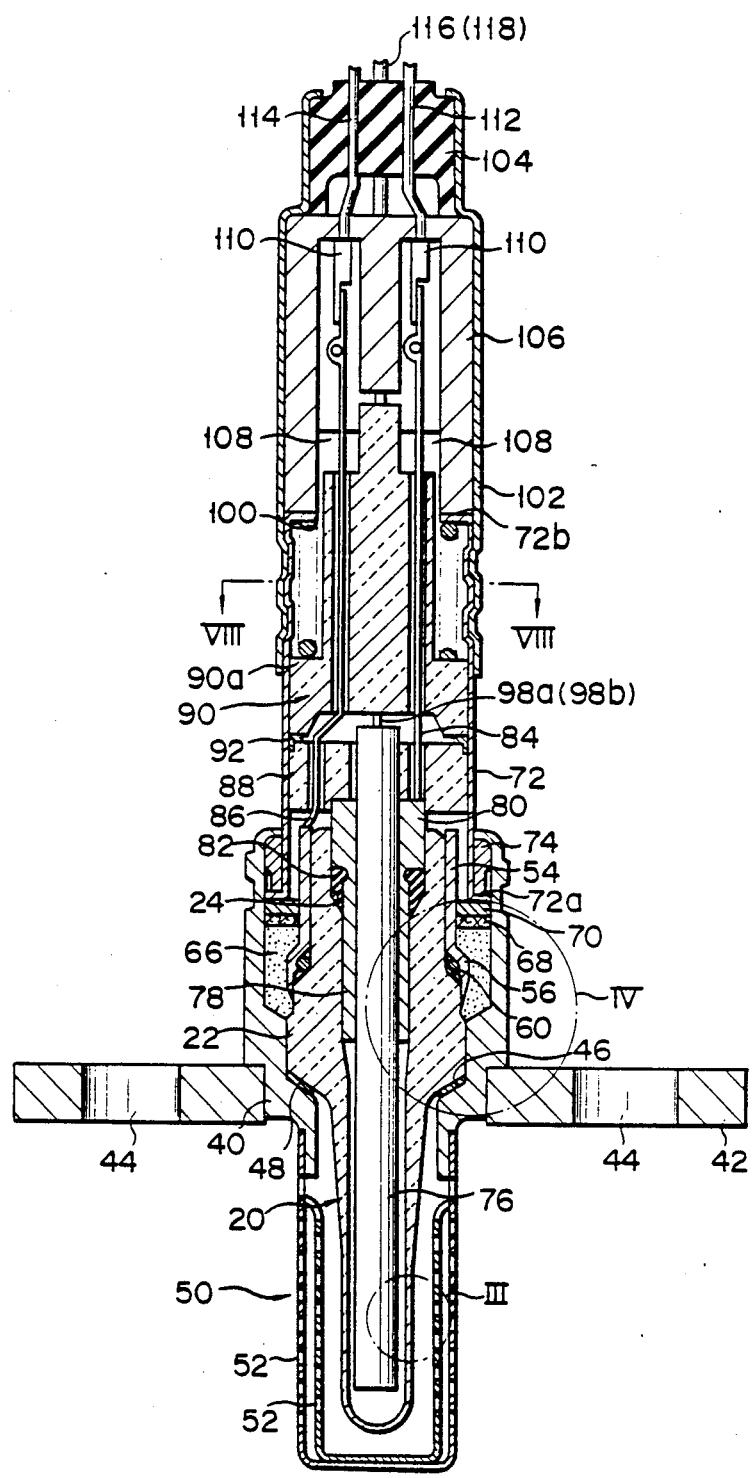
FIG. 1 is a vertical sectional view of an oxygen sensor according to one embodiment of the present invention.
Figure 5:
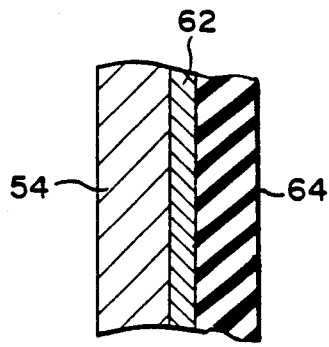
FIG. 5 is an enlarged sectional view showing part of a pipe member.

Referring now to FIG. 1, there is shown an outline of an oxygen sensor according to one embodiment of the present invention. The oxygen sensor is provided with a solid electrolytic element 20. The element 20 is in the form of a tumbler open at one end and closed at the other end. The element 20 is designed so that if its outer and inner surfaces are exposed to a subject gas to be measured and a reference gas such as the atmosphere, respectively, an electromotive force responsive to the oxygen content of the subject gas is produced between the outer and inner surfaces. For example, the element 20 is made of an oxygen-ion-conductive metal oxide whose electric resistance is reduced as it is heated. The oxygen-ion-conductive metal oxide used may, for example, be a fine sintered compact which consists of a solid solution containing 95 mol % of $ZrO_2$ and 5 mol % of $Yb_2O_3$. A flange 22 is formed integrally on the central portion of the outer peripheral surface of the element 20. An annular stepped portion 24 is formed in the inner peripheral surface of the element 20 on the open end side thereof.

As shown in FIG. 2, a first electrode 26 formed of porous platinum film is fixed to a part of the outer peripheral surface of the element 20 on the closed end side thereof. The area of the first electrode 26 ranges from 20 $mm^2$ to 100 $mm^2$, while the thickness of that portion of the element 20 fitted with the first electrode 26 ranges from 0.2 mm to 0.8 mm. A second electrode 28 formed of porous platinum film like the first electrode 26 is fixed to the inner peripheral surface of the element 20. The second electrode 28, as shown in FIG. 2, covers the whole inner peripheral surface of the element 20. Instead of being made of platinum, the first and second electrodes 26 and 28 may be formed from an alloy or a material capable of catalytic action, such as palladium.

As shown in FIG. 2, an electrical insulating layer 30 formed of a heat resisting ceramic material covers the whole outer peripheral surface of the element 20 located below the flange 20 excepting the region corresponding to the first electrode 26. Further, a filmy metal lead 32 is formed on the insulating layer 30, electrically connected to the first electrode 26. The metal lead 32 is formed also on the outer peripheral surface of the element 20, extending beyond the flange 22.

There will now be described processes for forming the first electrode 26, the insulating layer 30, and the metal lead 32 on the outer peripheral surface of the element 20. First, that portion of the outer peripheral surface of the element 20 on which the first electrode 26 is to be fixed is covered with a mask member. Thereafter, a heat resisting insulating ceramic material, such as alumina or alumina-magnesia spinel, is put on the outer peripheral surface of the element 20 by plasma spraying, thus forming the insulating layer 30. The insulating layer 30 is about 100 microns in thickness. After it is coated with the insulating layer 30, the mask member is removed from the element 20, and the outer peripheral surface of the element 20 and the insulating layer 30 are coated with platinum or the like by chemical plating or pasting. Consequently, as best seen in FIG. 3, the first electrode 26 is formed on the outer peripheral surface of the element 20 having so far been covered with the mask member, and the metal lead 32 is formed at the same time. Thus, the metal lead 32 covers the whole region of the insulating layer 30, and is electrically insulated from the element 20.

Further, the first electrode 26 and the metal lead 32 are covered with a gas-diffusible resistance layer 36, excepting that portion of the flange 22 of the element 20 which is coated with the metal lead 32. The gas-diffusible resistance layer 26 is formed by plasma-spraying a porous, insulating ceramic material, such as $Al_2O_3$ or $ZrO_2$, on the outer surfaces of the first electrode 26 and the metal lead 32. The gas-diffusible resistance layer 36 may be formed by bonding a preformed ceramic filter to the surfaces, as well as by plasma spraying.

That portion of the flange 22 of the element 20 covered with the metal lead 32 is coated with an insulating layer 38 formed of a heat resisting metal oxide. As best seen from FIG. 4, the insulating layer 38 extends so as to cover a part of the gas-diffusible resistance layer 36. The insulating layer 38 is a coating of e.g., about 100-micron which is formed by plasma-spraying a heat resisting oxide, such as $Al_2O_3$ or $MgO_3$-$Al_2O_3$.

As shown in FIG. 1, the solid electrolytic element 20 is held in a cylindrical metallic holder 40. A ring-shaped seat portion 46 is formed on the inner peripheral surface of the holder 40, and the flange 22 of the element 20 rests on a metal ring packing 48 which is fitted on the ring-shaped seat portion 46, as shown in FIG. 4. Since the outer peripheral surface of the flange 22 of the element 20 is coated with the insulating layer 38, as mentioned before, the holder 40 and the lead 32 are electrically insulated by the insulating layer 38.

A mounting flange 42 is fixed on the outer peripheral surface of the holder 40, having a plurality of bolt holes 44 therein. Thus, the holder 40 can be attached to an exhaust pipe of an engine by means of the mounting flange 42 and bolts inserted in the bolt holes 44. When the holder 40 with the element 20 therein is attached to the exhaust pipe in this manner, the lower portion of the element 20 projects from the holder 40 so that the element 20 can be exposed to exhaust gas flowing through the exhaust pipe. The holder 40 is fitted with a protective cover 50 for covering that portion of the element 20 which projects into the exhaust pipe. The protective cover 50, as shown in FIG. 1, has a double-wall structure in which each frame of a double-frame wall is formed with a plurality of apertures 52 through which the exhaust gas is introduced into the space inside the protective cover 50.

The open end portion of the element 20 is fitted in a conductive metallic pipe member 54. A widened portion 56 is formed integrally at one end portion of the pipe member 54 which is located on the side of the flange 22 of the element 20. The inner surface of the extreme end of the widened portion 56 is in plane contact with the lead 32 which extends beyond the flange 22 of the element 20 toward the open end side of the element 20. As shown in FIG. 4, moreover, a conductive metal ring 60 is disposed in an annular space 58 which is defined by the inner peripheral surface of the widened portion 56 of the pipe member 54 and the outer peripheral surface of the element 20. The pipe member 54 and the lead 32 of the element 20 are electrically connected through the metal ring 60.

An electrical insulating layer 64 is fitted on that portion of the outer peripheral surface of the pipe member 54 above the widened portion 56 by means of a bonding material 62. The bonding material 62 constitutes a coating of about 30-micron which is formed by plasma-spraying a thermal expansion regulating material, such as Ni-Al$_2$O$_3$. The insulating layer 64 is a coating of about 100-micron which is formed by plasma-spraying a heat resisting insulating oxide, such as Al$_2$O$_3$, ZrO$_3$ or MgO-Al$_2$O$_3$.

A seal member 66 is interposed between the inner peripheral surface of the holder 40 and the respective outer peripheral surfaces of the insulating layer 64, the widened portion 56, and the element 20, located above the flange 22 of the element 20 as illustrated. The seal member 66 is formed by compacting a powdered electrical insulating material such as talc. An asbestos ring 68 and a metal pad 70 are successively arranged on the seal member 66.

One end portion of a metal pipe 72 is inserted in the holder 40 so as to surround the pipe member 54. The metal pipe 72 is formed at one end with a flange portion 72a, which abuts against the metal pad 70. A metallic spacer ring 74 is interposed between the outer peripheral surface of the one end of the metal pipe 72 and the inner peripheral surface of the holder 40, abutting against the flange portion 72a. The upper end portion, as illustrated, of the holder 40 is cooled and crimped in a direction such that the spacer ring 74 is pressed downward. As a result, the pipe member 54 is pressed down through the medium of the spacer ring 74, metal pad 70, asbestos ring 68, seal member 66, and widened portion 56. Thus, electrical contact between the pipe member 54 and the lead 32 by means of the metal ring 60 can be ensured.

A rod-shaped ceramic heater 76 is inserted into the element 20. The ceramic heater 76 consists, for example, of a hollow insulator formed by extrusion molding, and a heater element including a ceramic film formed by the doctor blade method and filmy heater wires screen-printed on the ceramic film. The ceramic heater 76 is fabricated by winding the heater element around the insulator and then sintering them together. A metal stem 78 is disposed between the outer peripheral surface of the ceramic heater 76 and the inner peripheral surface of the element 20. A flange portion 80 is formed at the upper end portion, as illustrated, of the metal stem 78. A ring-shaped graphite 82 is disposed between the flange portion 80 and the stepped portion 24 of the element 20 so as to be in contact with both the second electrode 28 and the metal stem 78. Thus, the metal stem 78 and the second electrode 28 are electrically connected through the graphite 82. The metal stem 78 is bonded to the outer peripheral surface of the ceramic heater 76 by, e.g., silver-alloy brazing.

Figure 6:
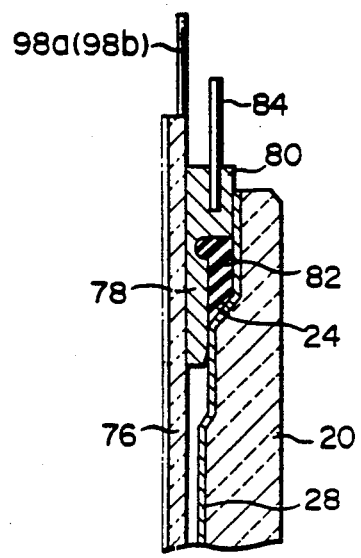
FIG. 6 is an enlarged sectional view showing the upper end portion of the solid electrolytic element.
Figure 7:
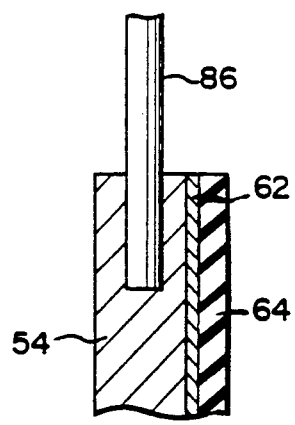
FIG. 7 is an enlarged sectional view showing the upper end portion of the pipe member.

A nickel lead wire 84 is connected to the upper end, as illustrated, of the metal stem 78. As shown in FIG. 6, one end of the lead wire 84 is buried in the upper end portion of the metal stem 78 and then brazed to the metal stem 78. As shown in FIG. 7, one end of another nickel lead 86 is buried in the upper end portion of the pipe member 54 and then brazed to the pipe member 54.

The lead wires 84 and 86 and the upper end portion of the ceramic heater 76 extend upward through a first insulator member 88 which is disposed inside the metal pipe 72. The first insulator member 88 is ring-shaped and formed from Al$_2$O$_3$. The ceramic heater 76 penetrates a center hole in the first insulator member 88. Inside the metal pipe 72, a second insulator member 90 of the same material as the first insulator member 88 is disposed over the first insulator member 88. The second insulator member 90 is in the form of a stepped cylinder whose end portion on the side of the first insulator member 88 is increased in diameter. A nickel ring packing 92 is interposed between the first and second insulator members 88 and 90.

Figure 8:
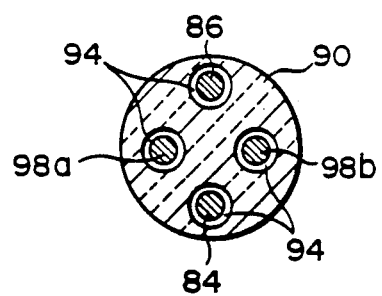
FIG. 8 is a sectional view taken along line VIII—VIII of FIG. 1.

As shown in FIG. 8, the second insulator member 90 is formed with four axial penetrating holes 94. The lead wires 84 and 86 and nickel lead wires 98a and 98b connected to the heater wires of the ceramic heater 76 are individually passed through the penetrating holes 94.

A flange portion 72b extends inwardly at the upper end, as illustrated, of the metal pipe 72. A compression coil spring 100 is disposed between the flange portion 72b and the widened portion 90a of the second insulator member 90. Thus, by the spring 100, the first insulator member 88 is pressed against the flange portion 80 of the metal stem 78 through the medium of the second insulator member 90 and the ring packing 92.

Figure 9:
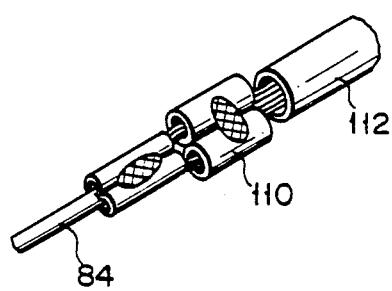
FIG. 9 is a perspective view showing a connector for lead wires.

A dust pipe 102 is connected to the upper end portion of the metal pipe 72 by crimping. A bush 104 is disposed inside the upper end portion of the dust pipe 102, and is fixed by crimping the upper end portion of the dust pipe 102. Inside the dust pipe 102, a spacer 106, formed from fluorine resin, is interposed between the bush 104 and the flange portion 72b of the metal pipe 72. Four penetrating holes 108 are bored axially through the spacer 106. Only two of the penetrating holes 108 are shown in FIG. 1. The lead wires 84, 86, 98a and 98b are individually passed through the penetrating holes 108 of the spacer 106, and are connected to lead wires 112, 114, 116 and 118, respectively, by means of connectors 110, as shown in detail in FIG. 9. The lead wires 112, 114, 116 and 118 are led out through the bush 104.

The operating mode of the above described oxygen sensor will now be described.

The lead wires 114 and 112 are connected to the cathode and anode, respectively, of a power source (not shown). A predetermined voltage is applied between the first and second electrodes 26 and 28. In this state, oxygen molecules in the exhaust gas reaching the first electrode 26 through the gas-diffusible resistance layer 36 are supplied with electrons from the first electrode 26 to be converted into oxygen ions. These oxygen ions diffuse into the element 20 to reach the second electrode 28, where they release electrons to return to oxygen molecules. As a result, an electric current flows between the first and second electrodes 26 and 28. The oxygen molecules produced at the second electrode 28 pass through a penetrating hole in the ceramic heater 76 and are discharged into the atmosphere through gaps between the several components.

In the process of diffusion of the oxygen ions inside the element 20, the current flowing between the first and second electrodes 26 and 28 increases if the voltage applied between the two electrodes 26 and 28 is gradually increased on condition that the gas-diffusible resistance layer 36 has a thickness greater than a predetermined value, e.g., 300 microns, and that the first electrode 26 has a fixed area within a range from 20 mm$^2$ to 100 mm$^2$. If the voltage exceeds a certain level, however, a region will be created in which the value of the current flowing between the first and second electrodes 26 and 28 undergoes no changes, on account of the influence of the gas-diffusible resistance layer 36, even though the voltage is further increased. Namely, a saturated current flows through the first and second electrodes 26 and 28. The saturated current I1 may be expressed as follows:

$$Il \simeq \frac{4F \times DO_2}{R \times T} \times \frac{S}{L} \times PO_2$$

Here
- F: Faraday constant,
- R: gas constant,
- $DO_2$: diffusion constant of oxygen molecules,
- T: absolute temperature of element,
- S: area of first electrode,
- L: effective diffusion length of gas-diffusible resistance layer,
- $PO_2$: partial oxygen pressure.

As is evident from the above expression, the saturated current Il changes only with the change of the oxygen content or partial oxygen pressure of the exhaust gas if the temperature of the element 20 is kept constant by the ceramic heater 76. Thus, with a voltage higher than a predetermined level for the production of the saturated current applied between the first and second electrodes 26 and 28, the oxygen content of the exhaust gas can be detected by measuring the saturated current flowing through the first and second electrodes 26 and 28.

According to the oxygen sensor described above, the drawbacks of the prior art oxygen sensors can be eliminated for the improvement of durability. As shown in FIG. 4, the space 58 for the electrical junction between the pipe member 54 and the lead 32 is separated from the seal member 66 by the widened portion 56 of the pipe member 54. Therefore, powder from the seal member 66 is prevented from penetrating the space 58 and cannot cut the electrical connection between the pipe member 54 and the lead 32. Thus, the operation of the oxygen sensor can be improved in reliability.

Since the insulating layer 64 is formed on the outer peripheral surface of the pipe member 54, electrical insulation between the pipe member 54 and the holder 40 can further be ensured. Accordingly, the sensing capability of the oxygen sensor can be improved, as it is less affected by noises from the engine body.

Figure 10:
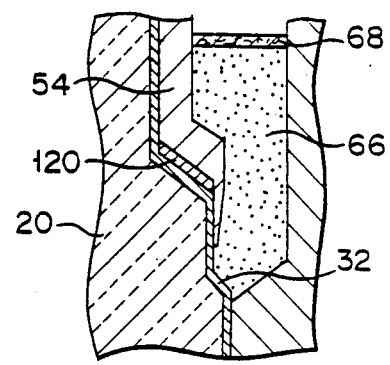
FIG. 10 is a sectional view showing a modified example of electrical connection between the pipe member and a lead.
Figure 11:
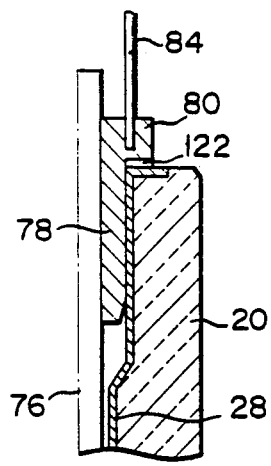
FIG. 11 is a sectional view showing a modified example of electrical connection between a lead wire and a second electrode.
Figure 12:
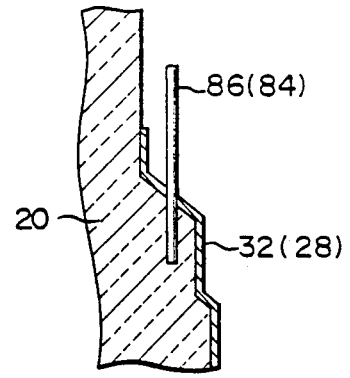
FIG. 12 is a sectional view showing a modified example of electrical connection between a lead wire and the lead.

The present invention is not limited to the embodiment described above. FIGS. 10, 11 and 12 show various modified examples.

Referring to FIG. 10, there is shown an example in which the pipe member 54 and the lead 32 are joined by means of a brazing alloy 120 instead of using the metal ring 60 for electrically connecting them.

Referring to FIG. 11, there is shown an example in which the metal stem 78 and the second electrode 28 are connected by means of a brazing alloy 122 instead of using the graphite 82 for electrically connecting them.

Referring to FIG. 12, moreover, there is shown an example in which the lead wire 86 (84), with its extreme end buried in the element 20, is brazed to the lead 32 (second electrode 28). It is to be understood that, also in this case, the junction between the lead wire 86 and the lead 32 is located in the space 58 defined by the widened portion 56 of the pipe member 54.

In the foregoing embodiment, the oxygen content of the exhaust gas is detected by the use of the oxygen sensor. Alternatively, however, the theoretical air-fuel ratio of the air-fuel mixture used in the engine may be detected on the basis of a measurement of an electromotive force produced between the first and second electrodes 26 and 28 by the difference in oxygen content between the exhaust gas and the atmosphere.

Further, the oxygen sensor of the present invention may be applied to the control of air supply in, e.g., the combustion system of a blast furnace, as well as to the detection of the oxygen content of the exhaust gas of an engine.

What is claimed is:

1. An oxygen sensor for detecting the oxygen content of a subject gas to be measured, comprising:
    a solid electrolytic element formed of an oxygen-ion-conductive metal oxide and having the shape of a tumbler closed at one end and open at the other end, the outer and inner peripheral surfaces of the solid electrolytic element being exposed to the subject gas and a reference gas, respectively;
    a first electrode fixed to the outer peripheral surface of the solid electrolytic element on one end side thereof;
    a second electrode fixed to the inner peripheral surface of the solid electrolytic element;
    a lead put on the outer peripheral surface of the solid electrolytic element in an electrically insulated relation and electrically connected to the first electrode;
    a metallic holder surrounding the other end portion of the solid electrolytic element to hold the same, the holder being electrically insulated from the first electrode;
    a conductive member disposed between the outer peripheral surface of the solid electrolytic element and the inner peripheral surface of the holder creating a gap between the conductive member and the holder, and electrically connected to the lead;
    a seal member for filling up the gap between the conductive member and the holder, the seal member being formed by compacting a powdered electrical insulating material into the gap; and
    partitioning means for separating a junction between the lead and the conductive member from the seal member.

2. The oxygen sensor according to claim 1, wherein the conductive member includes a pipe member disposed between the outer peripheral surface of the solid electrolytic element and the seal member, and a junction for electrically connecting one end of the pipe member on the side of the closed end of the solid electrolytic element with the lead, and the partitioning means includes a partition wall extending from one end of the pipe member and defining a space for housing the junction between the outer peripheral surface of the solid electrolytic element and the seal member.

3. The oxygen sensor according to claim 2, wherein the partition wall is in the form of a ring integrally extending from one end of the pipe member and defines an annular space surrounding the outer peripheral surface of the solid electrolytic element.

4. The oxygen sensor according to claim 3, wherein the lead surrounds the outer peripheral surface of the solid electrolytic element, and the junction includes a conductive metal ring electrically connecting one end of the pipe member and the lead.

5. The oxygen sensor according to claim 3, wherein the lead surrounds the outer peripheral surface of the solid electrolytic element, and the junction is a brazed portion formed of a conductive material connecting one end of the pipe member and the lead.

6. The oxygen sensor according to claim 2, wherein an electrical insulating layer is formed on the outer peripheral surface of the pipe member.

* * * * *